United States Patent
Hammer et al.

(10) Patent No.: US 7,488,866 B2
(45) Date of Patent: Feb. 10, 2009

(54) GRO-1 HERBICIDE RESISTANCE GENE AND METHODS FOR ITS USE

(75) Inventors: Philip E. Hammer, Cary, NC (US);
Todd K. Hinson, Rougemont, NC (US);
Amy Elizabeth Shekita, Cary, NC (US)

(73) Assignee: Athenix Corporation, Research Triangle Park, NC (US)

( * ) Notice: Subject to any disclaimer, the term of this patent is extended or adjusted under 35 U.S.C. 154(b) by 240 days.

(21) Appl. No.: 11/312,866

(22) Filed: Dec. 20, 2005

(65) Prior Publication Data
US 2006/0150269 A1 Jul. 6, 2006

Related U.S. Application Data

(60) Provisional application No. 60/638,655, filed on Dec. 22, 2004.

(51) Int. Cl.
*C12N 15/82* (2006.01)
*C12N 15/52* (2006.01)

(52) U.S. Cl. .................... 800/300; 435/320.1; 435/419; 435/252.3; 536/23.2; 800/288; 800/298

(58) Field of Classification Search ........................ None
See application file for complete search history.

(56) References Cited

OTHER PUBLICATIONS

NCBI Database Report for Accession No. NP_104404.
NCBI Database Report for Accession No. NP_355517.
NCBI Database Report for Accession No. NP_437298.
NCBI Database Report for Accession No. NP_682771.
NCBI Database Report for Accession No. ZP_00673804.

*Primary Examiner*—David H Kruse
(74) *Attorney, Agent, or Firm*—Alston & Bird LLP

(57) ABSTRACT

Compositions and methods for conferring herbicide resistance to bacteria, plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed bacteria, plants, plant cells, tissues, and seeds. In particular, isolated nucleic acid molecules corresponding to glyphosate resistant nucleic acid sequences are provided. Additionally, amino acid sequences corresponding to the polynucleotides are encompassed. In particular, the present invention provides for isolated nucleic acid molecules comprising a nucleotide sequence encoding the amino acid sequence shown in SEQ ID NO:3 or the nucleotide sequence set forth in SEQ ID NO:1, 2, or 4.

16 Claims, 1 Drawing Sheet

FIG. 1

SEQUENCE LISTING

<160> NUMBER OF SEQ ID NOS: 9

<210> SEQ ID NO 1
<211> LENGTH: 831
<212> TYPE: DNA
<213> ORGANISM: Rhizobium sp.
<220> FEATURE:
<221> NAME/KEY: CDS
<222> LOCATION: (1)...(831)

<400> SEQUENCE: 1

```
atg aac aac gat agt ttc gag ctg aag ttc tgg ggc gtg cgg ggt agc      48
Met Asn Asn Asp Ser Phe Glu Leu Lys Phe Trp Gly Val Arg Gly Ser
1               5                   10                  15 atc cct gta tcg gga ccg gaa ttt gag cgg tac ggc ggc aat acg tcg      96
Ile Pro Val Ser Gly Pro Glu Phe Glu Arg Tyr Gly Gly Asn Thr Ser
            20                  25                  30 tgc att gag tta agg cat gaa ggc agg cat atc ttg ttc gac gcc ggg     144
Cys Ile Glu Leu Arg His Glu Gly Arg His Ile Leu Phe Asp Ala Gly
        35                  40                  45 acc ggt ttg cgc gaa gcg gcc gcg tct ctt gcg aag gaa ggg gtt cga     192
Thr Gly Leu Arg Glu Ala Ala Ala Ser Leu Ala Lys Glu Gly Val Arg
50                  55                  60 aat atc gat ctc ttc ttc acc cac tcg cat tac gat cat att atc ggc     240
Asn Ile Asp Leu Phe Phe Thr His Ser His Tyr Asp His Ile Ile Gly
65                  70                  75                  80 ctg cct ttc ttc aac gcg atc tat gat ccg cgc gtc agc gta gat ctg     288
Leu Pro Phe Phe Asn Ala Ile Tyr Asp Pro Arg Val Ser Val Asp Leu
                85                  90                  95 tgg tcc ggg cat ctg gcc ggc aag acg aca act cgg cag ttg atc ggt     336
Trp Ser Gly His Leu Ala Gly Lys Thr Thr Thr Arg Gln Leu Ile Gly
            100                 105                 110 caa ttt atg aga ccg ccc tgg ttt cct gtc gaa ccc gat atc tgt cgc     384
Gln Phe Met Arg Pro Pro Trp Phe Pro Val Glu Pro Asp Ile Cys Arg
        115                 120                 125 gcc acg atg aat ttc cgc gat ttc gcc gcc agc gat acg ctg aag ccg     432
Ala Thr Met Asn Phe Arg Asp Phe Ala Ala Ser Asp Thr Leu Lys Pro
    130                 135                 140 cat cca ggt atc gtc att cat acc gcc agg ctg aat cat ccg ggc ggc     480
His Pro Gly Ile Val Ile His Thr Ala Arg Leu Asn His Pro Gly Gly
145                 150                 155                 160 tgc atc ggt tat cgc atc gag tgg tcc ggc cgg atc atc gcc atg gtc     528
Cys Ile Gly Tyr Arg Ile Glu Trp Ser Gly Arg Ile Ile Ala Met Val
                165                 170                 175 tac gat acg gaa cat gtg gcc ggt aaa atc gat gag acg gct ctg gag     576
Tyr Asp Thr Glu His Val Ala Gly Lys Ile Asp Glu Thr Ala Leu Glu
            180                 185                 190 ttg atg gcc ggt gcg gat ctt gcc atc tat gac gcg acc tat ctc gaa     624
Leu Met Ala Gly Ala Asp Leu Ala Ile Tyr Asp Ala Thr Tyr Leu Glu
        195                 200                 205 tcg gaa atg cag aaa tac ctg ggc ttt ggc cac tcc acg tgg gag gaa     672
Ser Glu Met Gln Lys Tyr Leu Gly Phe Gly His Ser Thr Trp Glu Glu
    210                 215                 220 ggc att aag ctt gcc gag aag gct ggc gcc aaa cga ctg gcg ctt ttc     720
Gly Ile Lys Leu Ala Glu Lys Ala Gly Ala Lys Arg Leu Ala Leu Phe
225                 230                 235                 240 cat cac gct ccg gga cgc acc gat cgc gaa ctg gac gag atg cag cgc     768
His His Ala Pro Gly Arg Thr Asp Arg Glu Leu Asp Glu Met Gln Arg
                245                 250                 255
```

```
gat gcg cag aag cgt ttt ccg caa gcc ttc ttc gcg ttt gat ggc cag      816
Asp Ala Gln Lys Arg Phe Pro Gln Ala Phe Phe Ala Phe Asp Gly Gln
        260                 265                 270 tcg ctg caa ctc tga                                                   831
Ser Leu Gln Leu *
        275

<210> SEQ ID NO 2
<211> LENGTH: 831
<212> TYPE: DNA
<213> ORGANISM: Brevundimonas vesicularis
<220> FEATURE:
<221> NAME/KEY: CDS
<222> LOCATION: (1)...(831)

<400> SEQUENCE: 2 atg aac aac gat agt ttc gag ctg aag ttc tgg ggc gtg cgg ggt agc       48
Met Asn Asn Asp Ser Phe Glu Leu Lys Phe Trp Gly Val Arg Gly Ser
1               5                   10                  15 atc cct gta tcg gga ccg gaa ttt gag cgg tac ggc ggc aat acg tcg       96
Ile Pro Val Ser Gly Pro Glu Phe Glu Arg Tyr Gly Gly Asn Thr Ser
                20                  25                  30 tgc att gag tta agg cat gaa ggc agg cat atc ttg ttc gac gcc ggg      144
Cys Ile Glu Leu Arg His Glu Gly Arg His Ile Leu Phe Asp Ala Gly
            35                  40                  45 acc ggt ttg cgc gaa gcg gcc gcg tct ctt gcg aag gaa ggg gtc cgg      192
Thr Gly Leu Arg Glu Ala Ala Ala Ser Leu Ala Lys Glu Gly Val Arg
        50                  55                  60 aat atc gat ctc ttc ttc acc cac tcg cat tat gat cac att atc ggc      240
Asn Ile Asp Leu Phe Phe Thr His Ser His Tyr Asp His Ile Ile Gly
65                  70                  75                  80 ctg cct ttc ttc aac gcg atc tat gat ccg cgc gtc agc gta gat ctg      288
Leu Pro Phe Phe Asn Ala Ile Tyr Asp Pro Arg Val Ser Val Asp Leu
                85                  90                  95 tgg tcc ggg cat ctt gcc ggc aag acg acc acg cgg cag ctg atc ggt      336
Trp Ser Gly His Leu Ala Gly Lys Thr Thr Thr Arg Gln Leu Ile Gly
            100                 105                 110 caa ttc atg cga ccg ccc tgg ttt cct gtc gaa ccc gat atc tgt cgc      384
Gln Phe Met Arg Pro Pro Trp Phe Pro Val Glu Pro Asp Ile Cys Arg
        115                 120                 125 gcc acg atg aat ttc cgc gat ttc gcg gcc agc gat acg ctg aaa ccg      432
Ala Thr Met Asn Phe Arg Asp Phe Ala Ala Ser Asp Thr Leu Lys Pro
    130                 135                 140 cat cca ggt atc gtc att cat acc gcc agg ctg aat cat ccg ggc ggc      480
His Pro Gly Ile Val Ile His Thr Ala Arg Leu Asn His Pro Gly Gly
145                 150                 155                 160 tgc atc ggt tat cgc atc gag tgg tcc ggc cgg atc atc gcc atg gtc      528
Cys Ile Gly Tyr Arg Ile Glu Trp Ser Gly Arg Ile Ile Ala Met Val
                165                 170                 175 tat gat acg gaa cat gtg gcc ggc aaa atc gat gag acg gct ctg gag      576
Tyr Asp Thr Glu His Val Ala Gly Lys Ile Asp Glu Thr Ala Leu Glu
            180                 185                 190 ctg atg gcc ggt gcg gat ctt gcc atc tat gac gcg acc tat ctc gaa      624
Leu Met Ala Gly Ala Asp Leu Ala Ile Tyr Asp Ala Thr Tyr Leu Glu
        195                 200                 205 tcg gaa atg cag aaa tac ctg ggc ttt ggc cac tcc acg tgg gag gaa      672
Ser Glu Met Gln Lys Tyr Leu Gly Phe Gly His Ser Thr Trp Glu Glu
    210                 215                 220 ggc att aag ctt gcc gag aag gcc ggc gcc aaa cga ttg gcg ctt ttc      720
Gly Ile Lys Leu Ala Glu Lys Ala Gly Ala Lys Arg Leu Ala Leu Phe
225                 230                 235                 240
```

```
cat cat gct ccg gga cgc acc gac cgc gaa ctg gac gag atg cag cgc      768
His His Ala Pro Gly Arg Thr Asp Arg Glu Leu Asp Glu Met Gln Arg
            245                 250                 255 gat gcg cag aag cgt ttt ccg caa gcc ttc ttc gcg ttt gat ggc cag      816
Asp Ala Gln Lys Arg Phe Pro Gln Ala Phe Phe Ala Phe Asp Gly Gln
        260                 265                 270 tcg ctg cag ctc tga                                                   831
Ser Leu Gln Leu  *
        275
```

<210> SEQ ID NO 3
<211> LENGTH: 276
<212> TYPE: PRT
<213> ORGANISM: Brevundimonas vesicularis

<400> SEQUENCE: 3

```
Met Asn Asn Asp Ser Phe Glu Leu Lys Phe Trp Gly Val Arg Gly Ser
 1               5                  10                  15

Ile Pro Val Ser Gly Pro Glu Phe Glu Arg Tyr Gly Gly Asn Thr Ser
            20                  25                  30

Cys Ile Glu Leu Arg His Glu Gly Arg His Ile Leu Phe Asp Ala Gly
        35                  40                  45

Thr Gly Leu Arg Glu Ala Ala Ala Ser Leu Ala Lys Glu Gly Val Arg
    50                  55                  60

Asn Ile Asp Leu Phe Phe Thr His Ser His Tyr Asp His Ile Ile Gly
65                  70                  75                  80

Leu Pro Phe Phe Asn Ala Ile Tyr Asp Pro Arg Val Ser Val Asp Leu
                85                  90                  95

Trp Ser Gly His Leu Ala Gly Lys Thr Thr Thr Arg Gln Leu Ile Gly
            100                 105                 110

Gln Phe Met Arg Pro Pro Trp Phe Pro Val Glu Pro Asp Ile Cys Arg
        115                 120                 125

Ala Thr Met Asn Phe Arg Asp Phe Ala Ala Ser Asp Thr Leu Lys Pro
    130                 135                 140

His Pro Gly Ile Val Ile His Thr Ala Arg Leu Asn His Pro Gly Gly
145                 150                 155                 160

Cys Ile Gly Tyr Arg Ile Glu Trp Ser Gly Arg Ile Ile Ala Met Val
                165                 170                 175

Tyr Asp Thr Glu His Val Ala Gly Lys Ile Asp Glu Thr Ala Leu Glu
            180                 185                 190

Leu Met Ala Gly Ala Asp Leu Ala Ile Tyr Asp Ala Thr Tyr Leu Glu
        195                 200                 205

Ser Glu Met Gln Lys Tyr Leu Gly Phe Gly His Ser Thr Trp Glu Glu
    210                 215                 220

Gly Ile Lys Leu Ala Glu Lys Ala Gly Ala Lys Arg Leu Ala Leu Phe
225                 230                 235                 240

His His Ala Pro Gly Arg Thr Asp Arg Glu Leu Asp Glu Met Gln Arg
                245                 250                 255

Asp Ala Gln Lys Arg Phe Pro Gln Ala Phe Phe Ala Phe Asp Gly Gln
            260                 265                 270

Ser Leu Gln Leu
        275
```

<210> SEQ ID NO 4
<211> LENGTH: 831
<212> TYPE: DNA
<213> ORGANISM: Artificial Sequence -continued

```
<220> FEATURE:
<223> OTHER INFORMATION: Synthetic gro-1 sequence
<220> FEATURE:
<221> NAME/KEY: CDS
<222> LOCATION: (1)...(831)

<400> SEQUENCE: 4 atg aac aac gat agc ttc gag ctg aag ttc tgg ggc gtg cgc ggt agc     48
Met Asn Asn Asp Ser Phe Glu Leu Lys Phe Trp Gly Val Arg Gly Ser
 1               5                  10                  15 atc cct gtg tca gga ccg gaa ttt gag cgc tac ggc ggc aat acg tcc     96
Ile Pro Val Ser Gly Pro Glu Phe Glu Arg Tyr Gly Gly Asn Thr Ser
             20                  25                  30 tgc att gag ctc agg cac gaa ggc cgt cat atc ttg ttc gac gcc ggg    144
Cys Ile Glu Leu Arg His Glu Gly Arg His Ile Leu Phe Asp Ala Gly
         35                  40                  45 acc ggt ctc cgc gaa gcg gcc gcg tca ctt gcg aag gaa ggg gtg aga    192
Thr Gly Leu Arg Glu Ala Ala Ala Ser Leu Ala Lys Glu Gly Val Arg
 50                  55                  60 aat atc gat ctc ttc ttc acc cac tcc cat tac gat cat att atc ggc    240
Asn Ile Asp Leu Phe Phe Thr His Ser His Tyr Asp His Ile Ile Gly
 65                  70                  75                  80 ctg cct ttc ttc aac gcg atc tat gat ccg cgc gtg agc gtg gat ctg    288
Leu Pro Phe Phe Asn Ala Ile Tyr Asp Pro Arg Val Ser Val Asp Leu
                 85                  90                  95 tgg tca ggg cat ctg gcc ggc aag acg aca act cgg cag ttg atc ggt    336
Trp Ser Gly His Leu Ala Gly Lys Thr Thr Thr Arg Gln Leu Ile Gly
            100                 105                 110 caa ttt atg aga ccg ccc tgg ttt cct gtc gaa ccc gat atc tgc cgc    384
Gln Phe Met Arg Pro Pro Trp Phe Pro Val Glu Pro Asp Ile Cys Arg
        115                 120                 125 gcc acg atg aat ttc cgt gat ttc gcc gcc tca gat acg ctg aag ccg    432
Ala Thr Met Asn Phe Arg Asp Phe Ala Ala Ser Asp Thr Leu Lys Pro
    130                 135                 140 cat cct ggt atc gtg att cat acc gcc agg ctg aat cat ccg ggc ggc    480
His Pro Gly Ile Val Ile His Thr Ala Arg Leu Asn His Pro Gly Gly
145                 150                 155                 160 tgc atc ggt tat cgc atc gag tgg tca ggc cgg atc atc gcg atg gtc    528
Cys Ile Gly Tyr Arg Ile Glu Trp Ser Gly Arg Ile Ile Ala Met Val
                165                 170                 175 tac gat acg gaa cat gtg gcg ggc aaa atc gat gag acg gct ctg gag    576
Tyr Asp Thr Glu His Val Ala Gly Lys Ile Asp Glu Thr Ala Leu Glu
            180                 185                 190 ttg atg gcc ggt gcg gat ctt gcc atc tat gac gcg acc tat ctc gaa    624
Leu Met Ala Gly Ala Asp Leu Ala Ile Tyr Asp Ala Thr Tyr Leu Glu
        195                 200                 205 tca gaa atg caa aag tac ctg ggc ttt ggc cac tca acg tgg gag gaa    672
Ser Glu Met Gln Lys Tyr Leu Gly Phe Gly His Ser Thr Trp Glu Glu
    210                 215                 220 ggc att aag ctg gcc gag aag gct ggc gcc aaa cgc ctg gcg ctt ttc    720
Gly Ile Lys Leu Ala Glu Lys Ala Gly Ala Lys Arg Leu Ala Leu Phe
225                 230                 235                 240 cat cac gct ccg gga cgc acc gat cgc gaa ctg gac gag atg caa cgc    768
His His Ala Pro Gly Arg Thr Asp Arg Glu Leu Asp Glu Met Gln Arg
                245                 250                 255 gat gcg cag aag cgt ttt ccg caa gcc ttc ttc gcg ttt gat ggc cag    816
Asp Ala Gln Lys Arg Phe Pro Gln Ala Phe Phe Ala Phe Asp Gly Gln
            260                 265                 270 tca ctg caa ctc tga                                                831
Ser Leu Gln Leu *
        275
```

<210> SEQ ID NO 5
<211> LENGTH: 284
<212> TYPE: PRT
<213> ORGANISM: Mesorhizobium loti

<400> SEQUENCE: 5

Met Asp Asp Val Phe Leu Val Arg Phe Trp Gly Val Arg Gly Ser
1               5                   10                  15

Ile Ser Val Ser Gly Pro Glu Phe Ser Arg Tyr Gly Gly Asn Thr Ile
                20                  25                  30

Cys Ile Glu Met Arg Cys Gly Lys His Thr Leu Leu Phe Asp Ala Gly
            35                  40                  45

Ser Gly Leu Gln Pro Ala Gly Arg Ala Leu Arg Ala Ser Gly Val Thr
        50                  55                  60

Asp Phe Asp Leu Leu Phe Thr His Cys His Tyr Asp His Ile Ile Gly
65                  70                  75                  80

Leu Pro Phe Phe Ala Pro Ile Tyr Asp Arg Ser Val Lys Val Thr Leu
                85                  90                  95

Trp Ser Gly His Leu Ala Gly Arg Met Thr Thr Arg Gln Met Val Asp
            100                 105                 110

Glu Phe Met Gln Pro Pro Trp Phe Pro Val Lys Leu Glu Ile Cys Lys
        115                 120                 125

Ala Ser Leu Asp Cys Arg Asp Phe Val Ser Gly Asp Val Leu Arg Pro
    130                 135                 140

Arg Glu Gly Val Val Val Arg Thr Gly Ser Leu Val His Pro Gly Gly
145                 150                 155                 160

Cys Ile Gly Tyr Arg Val Glu Trp Gly Gly Arg Val Val Ala Val Ile
                165                 170                 175

Thr Asp Thr Glu His Glu Pro Asp Lys Leu Asp Gln Ala Val Leu Gly
            180                 185                 190

Leu Ile Glu Gly Ala Asp Leu Val Ile Tyr Asp Cys Thr Tyr Thr Glu
        195                 200                 205

Glu Glu Met Glu Arg Arg Ser Gly His Gly His Ser Thr Trp Gln Gln
    210                 215                 220

Gly Val Lys Leu Cys Glu Ala Ala Gly Ala Arg Gly Leu Ala Leu Phe
225                 230                 235                 240

His His Asp Pro Ala Arg Thr Asp Glu Glu Leu Asp Glu Ile Glu Lys
                245                 250                 255

Leu Ala Lys Asp Arg Phe Ala Gly Ala Phe Ala Ala Arg Asp Gly Gln
            260                 265                 270

Thr Leu Lys Phe Pro Val Ser Leu His Lys Lys Arg
        275                 280

<210> SEQ ID NO 6
<211> LENGTH: 292
<212> TYPE: PRT
<213> ORGANISM: Agrobacterium tumefaciens

<400> SEQUENCE: 6

Met Leu Leu Gly Cys Ala Met Ala Phe Asp Ser Asp Thr Arg Ser Arg
1               5                   10                  15

Glu Ser Asn Arg Asn Phe Arg Val Lys Ile Trp Gly Ala Arg Gly Thr
                20                  25                  30

Leu Pro Val Ser Gly Glu Asn Phe Arg Lys Tyr Gly Gly Asn Thr Ile
            35                  40                  45

```
Cys Ile Glu Val Arg Cys Gly Asp His Val Leu Leu Phe Asp Ala Gly
         50                  55                  60

Ser Gly Leu His Pro Ala Gly Leu Ala Leu Arg Ala Glu Gly Ile Thr
 65                  70                  75                  80

Asp Val Asn Leu Phe Ser His Cys His Tyr Asp His Ile Val Gly
                 85                  90                  95

Phe Pro Tyr Phe Lys Pro Phe Tyr Asn Ser Ser Asn Asp Val Ala Ile
                100                 105                 110

Trp Ser Gly His Leu Ala Gly Ser Met Thr Thr Arg Glu Met Leu Lys
                115                 120                 125

Asp Phe Met Ser Pro Pro Trp Phe Pro Val Pro Leu Glu Ile Cys Cys
        130                 135                 140

Ala Lys Ile Ala Thr Arg Asp Phe Lys Ala Gly Asp Val Leu Asp Val
145                 150                 155                 160

His Pro Gly Leu Ser Ile Arg Thr Gly Met Leu Asn His Pro Gly Asn
                165                 170                 175

Ala Ile Gly Tyr Arg Leu Asp Trp Glu Gly Lys Ser Leu Ala Ile Ile
                180                 185                 190

Thr Asp Thr Glu His Glu Pro Ser Ser Ile Asp Glu Thr Val Leu Asp
        195                 200                 205

Leu Ile Arg Asp Val Asp Leu Phe Leu Tyr Asp Ala Met Phe Thr Asp
210                 215                 220

Glu Met Gly Leu Tyr Arg Gly Tyr Gly His Ser Ser Trp Gln Gln
225                 230                 235                 240

Ala Ile Arg Leu Ala Lys Leu Ala Asp Ala Lys Asn Val Gly Phe Ile
                245                 250                 255

His His Ala Pro Ser Arg Ser Asp Glu Leu Asp Asp Ile Glu Lys
                260                 265                 270

Gln Ala Lys Ala Glu Phe Asn Gly Ala Phe Ala Ala Met Asp Gly Gln
                275                 280                 285

Val Ile Glu Ile
    290

<210> SEQ ID NO 7
<211> LENGTH: 276
<212> TYPE: PRT
<213> ORGANISM: Sinorhizobium meliloti

<400> SEQUENCE: 7

Met Gln Asp Asp Thr Phe Arg Val Lys Phe Trp Gly Val Arg Gly Ser
 1               5                  10                  15

Leu Pro Val Ser Gly Glu Gln Phe Leu His Tyr Gly Gly Asn Thr Pro
                20                  25                  30

Cys Ile Glu Ile Arg Cys Gly Lys Glu Val Leu Ile Phe Asp Ala Gly
         35                  40                  45

Ser Gly Leu Arg Glu Ala Gly Leu Ser Leu Met Ser Glu Gly Val Ser
 50                  55                  60

Glu Phe Asp Val Phe Phe Thr His Thr His Tyr Asp His Ile Ile Gly
 65                  70                  75                  80

Leu Pro Tyr Phe Lys Pro Ile Tyr Arg Cys Ser Ser Ala Val Arg Phe
                85                  90                  95

Trp Ser Gly His Leu His Gly Thr Met Ser Thr Ala Glu Met Ile Asn
                100                 105                 110

Glu Phe Met Arg Pro Pro Trp Phe Pro Val Gly Thr Gly Ile Cys Gln
```

```
                115                 120                 125
Ala Ser Leu Asp Thr Val Asp Phe Arg Pro Gly Glu Thr Leu Ser Pro
    130                 135                 140

Arg Lys Asp Val Ser Ile Arg Thr Met Ser Leu Val His Pro Gly Gly
145                 150                 155                 160

Cys Val Gly Tyr Arg Ile Glu Trp Gly Gly Arg Ala Val Ala Leu Val
                165                 170                 175

Tyr Asp Thr Glu His Glu Pro Gly Ile Leu Asp Pro Val Leu Leu Asp
            180                 185                 190

Phe Ile Ala Gly Ala Asp Leu Met Ile Tyr Asp Cys Thr Tyr Leu Glu
        195                 200                 205

Ser Glu Met Pro Thr Phe Arg Gly Tyr Gly His Ser Thr Gly Met His
    210                 215                 220

Gly Ser Gln Leu Ala Lys Ala Ala Gly Val Thr Arg Leu Ala Met Phe
225                 230                 235                 240

His His Asp Pro Ser Arg Thr Asp Ala Ala Leu Ala Ala Met Glu Gln
                245                 250                 255

Glu Val Gln Ala Phe Phe Ser Gly Ala Phe Ala Ala Cys Asp Arg Gln
            260                 265                 270

Val Ile Asp Leu
        275

<210> SEQ ID NO 8
<211> LENGTH: 316
<212> TYPE: PRT
<213> ORGANISM: Thermosynechococcus elongatus

<400> SEQUENCE: 8

Met Ile His Ile Thr Ser Gln Ala Cys Phe Leu Trp His Thr Thr Ile
1               5                   10                  15

Asn Lys Ile Cys Asn Arg Pro Met Phe Asn Pro Leu Thr Ile Arg Phe
            20                  25                  30

Trp Gly Val Arg Gly Ser Ile Pro Cys Pro Gly Ser His Thr Val Arg
        35                  40                  45

Tyr Gly Gly Asn Thr Pro Cys Val Glu Ile Gln Ala Asn Gly Gln Arg
    50                  55                  60

Ile Ile Leu Asp Gly Gly Thr Gly Leu Arg Val Leu Gly Glu His Leu
65                  70                  75                  80

Met Gly Gln Gln Pro Val Thr Ala His Leu Phe Phe Thr His Thr His
                85                  90                  95

Trp Asp His Ile Gln Gly Phe Pro Phe Phe Gln Pro Ala Phe Val Pro
            100                 105                 110

Gly Asn Gln Phe His Ile Tyr Ala Val Pro Gly Lys Asn Gly Gln Gly
        115                 120                 125

Ile Glu Arg Arg Leu Asn Asp Gln Met Leu His Pro Asn Phe Pro Val
    130                 135                 140

Pro Leu Gln Ile Met Gly Gly Asp Leu Arg Phe Tyr Asp Leu Glu Val
145                 150                 155                 160

Gly Glu Arg Val His Leu Gly Asp Gly Val Val Ser Asn Glu Ala
                165                 170                 175

Leu Asn His Pro Gly Gly Val Gly Tyr Arg Val Ser Trp Gln Gly
            180                 185                 190

Ile His Val Ala Tyr Ile Thr Asp Thr Glu His Leu Pro Asp Arg Leu
        195                 200                 205
```

```
His Pro Gly Ala Phe Ala Leu Ala Asp His Ala Asp Val Met Ile Tyr
    210                 215                 220

Asp Ala Thr Tyr Thr Asp Glu Glu Tyr Tyr His Pro Gln Gln Ser Lys
225                 230                 235                 240

Val Gly Trp Gly His Ser Thr Trp Gln Glu Ala Val Lys Leu Ala Gln
                245                 250                 255

Ala Ala Gln Val Lys Gln Leu Ile Leu Phe His His Asp Pro Ser His
            260                 265                 270

Asp Asp Asp Cys Leu Asp Arg Ile Gly Glu Leu Ala Arg Ala Gln Phe
        275                 280                 285

Pro Gln Thr Leu Leu Ala Arg Glu Gly Leu Ile Ile Ser Val Tyr Pro
    290                 295                 300

Asn Val Ile His Phe Pro Ala Thr Pro Gln Ala Ser
305                 310                 315

<210> SEQ ID NO 9
<211> LENGTH: 301
<212> TYPE: PRT
<213> ORGANISM: Trichodesmium erythraeum

<400> SEQUENCE: 9

Met Leu Ser Ser Glu Ser Ser Pro Ile Ser Gln Ser Glu Glu Thr
1               5                   10                  15

Ala Thr Pro Ser Asp Ser Leu Ser Thr Asp Phe Val Val Glu Phe Trp
                20                  25                  30

Gly Val Arg Gly Ser Ile Pro Thr Pro Gly Ser Ser Thr Val Arg Tyr
            35                  40                  45

Gly Gly Asn Thr Ser Cys Val Glu Met Arg Val Gly Glu Lys Arg Leu
        50                  55                  60

Ile Phe Asp Gly Gly Thr Gly Leu Arg Val Leu Gly Leu Glu Leu Leu
65                  70                  75                  80

Lys Glu Met Pro Val Glu Ala His Ile Phe Phe Ser His Thr His Trp
                85                  90                  95

Asp His Ile Gln Gly Phe Pro Phe Phe Val Pro Ala Phe Leu Pro Ile
            100                 105                 110

Asn Lys Phe His Ile Tyr Gly Ala Ile Ala Pro Asp Gly Thr Thr Ile
        115                 120                 125

Lys Glu Ser Leu Ser Asp Gln Met Val His Pro Asn Phe Pro Ile Pro
    130                 135                 140

Leu Gln Ile Met Gly Ser Gln Met Lys Phe Tyr Asp Phe Asn Asn Gly
145                 150                 155                 160

Asp Val Ile Gln Val Asp Asp Ile Glu Ile Glu Thr Ile Ser Leu Asn
                165                 170                 175

His Pro Asn Phe Ala Ile Gly Tyr Arg Val Cys Trp Gln Gly Lys Thr
            180                 185                 190

Val Val Tyr Cys Pro Asp Thr Glu His Tyr Glu Gly Tyr Phe Asp Glu
        195                 200                 205

Asn Ile Leu His Leu Ser Arg Asn Ala Asp Leu Leu Ile Tyr Asp Ala
    210                 215                 220

Thr Tyr Thr Asn Glu Glu Tyr Tyr Asp Val Lys Ser Pro Lys Ile Gly
225                 230                 235                 240

Leu Gly His Ser Thr Trp Glu Val Gly Val Glu Ile Ala Arg Lys Ala
                245                 250                 255

Gly Val Lys Gln Ile Ala Met Phe Gln His Asp Pro Gly His Asn Asp
            260                 265                 270
```

```
Asp Leu Leu Asp Glu Val Gln Val Ala Leu Gln Ser Ile Phe Ser Asn
        275                 280                 285

Gly Leu Val Ala Lys Glu Gly Met Thr Ile Pro Ile Leu
        290                 295             300
```

GRO-1 HERBICIDE RESISTANCE GENE AND METHODS FOR ITS USE

CROSS REFERENCE TO RELATED APPLICATION

This application claims the benefit of U.S. Provisional Application Ser. No. 60/638,655, filed Dec. 22, 2004, the contents of which are herein incorporated by reference in its entirety.

FIELD OF THE INVENTION

This invention provides novel genes encoding herbicide resistance, which are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases may have a high tolerance to glyphosate.

Plant cells resistant to glyphosate toxicity can be produced by transforming plant cells to express glyphosate-resistant EPSP synthases. A mutated EPSP synthase from *Salmonella typhimurium* strain CT7 confers glyphosate resistance in bacterial cells, and confers glyphosate resistance on plant cells (U.S. Pat. Nos. 4,535,060, 4,769,061, and 5,094,945). Thus, there is a precedent for the use of glyphosate-resistant bacterial EPSP synthases to confer glyphosate resistance upon plant cells.

An alternative method to generate target genes resistant to a toxin (such as an herbicide) is to identify and develop enzymes that result in detoxification of the toxin to an inactive or less active form. This development can be accomplished by identifying enzymes that encode resistance to the toxin in a toxin-sensitive test organism, such as a bacterium.

Castle et al. (WO 02/36782 A2) describe proteins (glyphosate N-acetyltransferases) that are described as modifying glyphosate by acetylation of a secondary amine to yield N-acetylglyphosate.

Barry et al. (U.S. Pat. No. 5,463,175) describe genes encoding an oxidoreductase (GOX), and states that GOX proteins degrade glyphosate by removing the phosphonate residue to yield amino methyl phosphonic acid (AMPA). This activity suggests that glyphosate resistance can also be conferred, at least partially, by removal of the phosphonate group from glyphosate. However, the resulting compound (AMPA) appears to provide reduced but measurable toxicity upon plant cells. Barry describes the effect of AMPA accumulation on plant cells as resulting in effects including chlorosis of leaves, infertility, stunted growth, and death. Barry (U.S. Pat. No. 6,448,476) describes plant cells expressing an AMPA-N-acetyltransferase (phnO) to detoxify AMPA.

Phophonates, such as glyphosate, can also be degraded by cleavage of C-P bond by a C-P lyase. Wacket et al. (1987) *J. Bacteriol.* 169:710-717 describe strains that utilize glyphosate as a sole phosphate source. Kishore et al. (1987) *J. Biol. Chem.* 262:12164-12168 and Shinabarger et al. (1986) *J. Bacteriol.* 168:702-707 describe degradation of glyphosate by C-P lyase to yield glycine and inorganic phosphate.

While several strategies are available for detoxification of toxins, such as the herbicide glyphosate, as described above, new activities capable of degrading glyphosate are useful. Novel genes and genes conferring glyphosate resistance by novel mechanisms of action would be of additional usefulness. Single genes conferring glyphosate resistance by formation of non-toxic products would be especially useful.

Thus, novel genes encoding resistance to herbicides are needed.

BRIEF SUMMARY OF THE INVENTION

Compositions and methods for conferring herbicide resistance to bacteria, plants, plant cells, tissues and seeds are provided. Compositions include nucleic acid molecules encoding sequences for herbicide resistance polypeptides, vectors comprising those nucleic acid molecules, and host cells comprising the vectors. Compositions comprising a coding sequence for a polypeptide that confers resistance or tolerance to glyphosate herbicides are provided, as well as antibodies to the polypeptides. Compositions of the present invention include synthetic nucleic acid molecules encoding herbicide resistance polypeptides. The coding sequences can be used in DNA constructs or expression cassettes for transformation and expression in organisms, including microorganisms and plants. Compositions also comprise transformed bacteria, plants, plant cells, tissues, and seeds. In addition, methods are provided for producing the polypeptides encoded by the synthetic nucleotides of the invention.

In particular, isolated nucleic acid molecules corresponding to herbicide resistance-conferring nucleic acid sequences are provided. Additionally, amino acid sequences corresponding to the polynucleotides are encompassed. In particular, the present invention provides for isolated nucleic acid molecules comprising a nucleotide sequence set forth in SEQ ID NO:1, 2, or 4, a nucleotide sequence encoding the amino acid sequence shown in SEQ ID NO:3, the herbicide resistance nucleotide sequence deposited in a bacterial host as Accession No. NRRL B-30787, as well as variants and fragments thereof. Nucleotide sequences that are complementary to a nucleotide sequence of the invention, or that hybridize to a sequence of the invention are also encompassed.

BRIEF DESCRIPTION OF FIGURES

Figure 1:
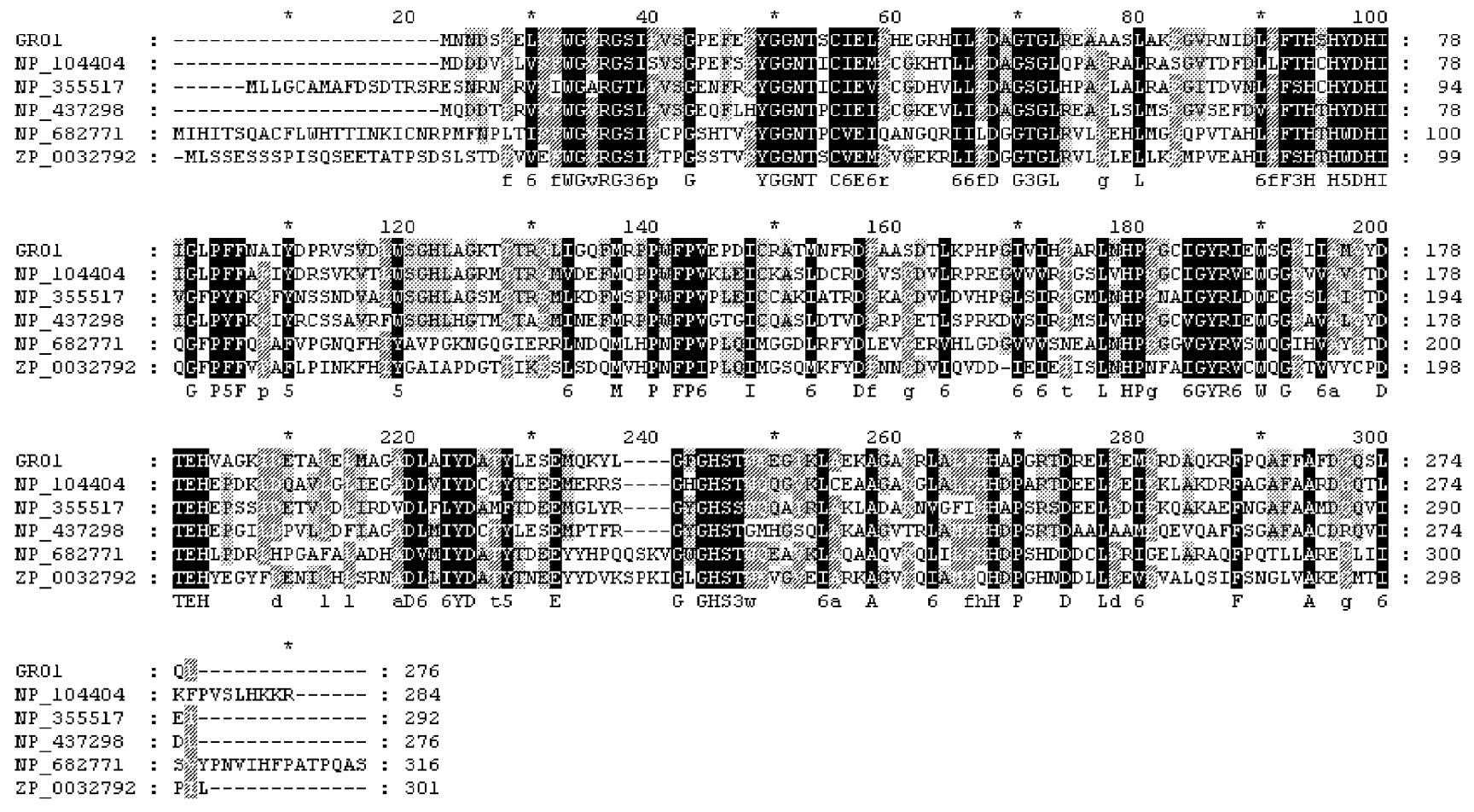

FIG. 1 shows an alignment of GRO-1 with a protein from *Mesorhizobium loti* (SEQ ID NO:5), a protein from *Agrobacterium tumefaciens* (SEQ ID NO:6), a protein from *Sinorhizobium meliloti* (SEQ ID NO:7), a protein from *Thermosynechococcus elongates* (SEQ ID NO:8), and a protein from *Trichodesmium erythraeum* (SEQ ID NO:9). The alignment shows the most highly conserved amino acid residues highlighted in black and highly conserved amino acid residues highlighted in gray.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is drawn to compositions and methods for regulating herbicide resistance in organisms, particularly in plants or plant cells. The methods involve transforming organisms with nucleotide sequences encoding an herbicide resistance protein of the invention. In particular, the nucleotide sequences of the invention are useful for preparing plants and microorganisms that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. More particularly, nucleotide sequences encoding all or part of the gene gro-1 and the amino acid sequences of the proteins encoded thereby are disclosed. The sequences find use in the construction of expression vectors for subsequent transformation into organisms of interest, as probes for the isolation of other herbicide resistance genes, as selectable markers, and the like.

Plasmids containing the herbicide resistance nucleotide sequences of the invention were deposited in the permanent collection of the Agricultural Research Service Culture Collection, Northern Regional Research Laboratory (NRRL) on Nov. 17, 2004, and assigned Accession No. NRRL B-30787. This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. § 1.808, sample(s) of the deposit with the NRRL. This deposit was made merely as a convenience for those of skill in the art and is not an admission that a deposit is required under 35 U.S.C. §112.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

Isolated Nucleic Acid Molecules, and Variants and Fragments Thereof

One aspect of the invention pertains to isolated nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOS:1, 2, and 4, the herbicide resistance nucleotide sequence deposited in a bacterial host as Accession No. NRRL B-30787, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the herbicide resistance protein encoded by these nucleotide sequences is set forth in SEQ ID NO:3. The invention also encompasses nucleic acid molecules comprising nucleotide sequences encoding partial-length herbicide resistance proteins, and complements thereof.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (for example, protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Nucleic acid molecules that are fragments of these herbicide resistance-encoding nucleotide sequences are also encompassed by the present invention. By "fragment" is intended a portion of the nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800 contiguous nucleotides, or up to the number of nucleotides present in a full-length herbicide resistance-encoding nucleotide sequence disclosed herein (for example, 831 nucleotides for SEQ ID NOS:1, 2, and 4) depending upon the intended use. By "contiguous" nucleotides is intended nucleotide residues that are immediately adjacent to one another.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance protein disclosed herein as SEQ ID NO:3. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250 contiguous amino acids, or up to the total number of amino acids present in a full-length herbicide resistance protein of the invention (for example, 277 amino acids for the protein of the invention).

Herbicide resistance proteins of the present invention are encoded by a nucleotide sequence sufficiently identical to the nucleotide sequence of SEQ ID NO:1, 2, or 4. The term "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to GDC-like nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) CABIOS 4:11-17. Such an algorithm is incorporated into the ALIGN program (version 2.0), which is part of the GCG sequence alignment software package (available from Accelrys, Inc. San Diego, Calif.). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode the herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for the ability to confer herbicide resistance activity to identify mutants that retain activity. Following mutagenesis, the encoded protein can be expressed in a cell, and the activity of the protein can be determined using standard assay techniques.

Using methods such as PCR, hybridization, and the like corresponding herbicide resistance sequences can be identified, such sequences having substantial identity to the sequences of the invention. See, for example, Sambrook and Russell (2001) *Molecular Cloning: A Laboratory Manual* (Cold Spring Harbor Laboratory Press, Cold Spring Harbor, N.Y.) and Innis, et al. (1990) *PCR Protocols: A Guide to Methods and Applications* (Academic Press, N.Y.).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, about 25, at least about 50, 75, 100, 125, 150, 175, 200, 250, 300, 350, or 400 consecutive nucleotides of herbicide resistance-encoding nucleotide sequence of the invention or a fragment or variant thereof. Methods for the preparation of probes for hybridization are generally known in the art and are disclosed in Sambrook and Russell, 2001, supra, and Sambrook et al. (1989) *Molecular Cloning: A Laboratory Manual* (2d ed., Cold Spring Harbor Laboratory Press, Cold Spring Harbor, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are at least about 10 nucleotides in length, or at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" is intended a protein having the amino acid sequence set forth in SEQ ID NO:3. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth in SEQ ID NO:3 and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NO:3. The invention encompasses other fragments, however, such as any fragment in the protein greater than about 10, 20, 30, 50, 100, 150, 200, 250, 300, 350, 400, 450, 500, 550, or 600 amino acids.

By "variants" is intended proteins or polypeptides having an amino acid sequence that is at least about 60%, 65%, about 70%, 75%, 80%, 85%, 90%, 91%, 92%, 93%, 94%, 95%, 96%, 97%, 98% or 99% identical to the amino acid sequence of SEQ ID NO:3. Variants also include polypeptides encoded by a nucleic acid molecule that hybridizes to the nucleic acid molecule of SEQ ID NO:1 or 2, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188,642, each of which are herein incorporated by reference in their entirety.

Antibodies to the polypeptides of the present invention, or to variants or fragments thereof, are also encompassed. Methods for producing antibodies are well known in the art (see, for example, Harlow and Lane (1988) "Antibodies: A Laboratory Manual," Cold Spring Harbor Laboratory, Cold Spring Harbor, N.Y.; U.S. Pat. No. 4,196,265).

Altered or Improved Variants

Bacterial genes, such as the gro-1 gene of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of gro-1 that confer herbicide resistance. Thus, the altered variants arising from the use of such start codons are contained in this invention. Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of gram-negative bacteria, or the endoplasmic reticulum of eukaryotic cells, the latter of which often results in glycosylation of the protein.

It is recognized that the DNA sequence of gro-1 may be altered by various methods, and that these alterations may result in DNA sequences encoding proteins with amino acid sequences different from that encoded by gro-1. This protein may be altered in various ways including amino acid substitutions, deletions, truncations, and insertions. Methods for such manipulations are generally known in the art. For example, amino acid sequence variants of the GRO-1 protein can be prepared by mutations in the DNA. This may also be accomplished by one of several forms of mutagenesis and/or in directed evolution. In some aspects, the changes encoded in the amino acid sequence will not substantially affect function of the protein. Such variants will possess the desired herbicide resistance activity. However, it is understood that the ability of GRO-1 to confer herbicide resistance may be improved by one use of such techniques upon the compositions of this invention. For example, one may express GRO-1 in host cells exhibit high rates of base misincorporation during DNA replication, such as XL-1 Red (Stratagene). After propagation in such strains, one can isolate the gro-1 DNA (for example by preparing plasmid DNA, or by amplifying by PCR and cloning the resulting PCR fragment into a vector), culture the gro-1 mutations in a non-mutagenic strain, and identify mutated gro-1 genes with improved resistance to an herbicide such as glyphosate, for example by growing cells in increasing concentrations of glyphosate and testing for clones that confer the ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

Provided herein are novel isolated genes that confer resistance to an herbicide. Also provided is an amino acid sequence of the GRO-1 protein. The protein resulting from translation of this gene allows cells to function in the presence of concentrations of an herbicide that are otherwise toxic to cells including plant cells and bacterial cells.

In one aspect of the invention, the gro-1 gene is useful as a marker to assess transformation of bacterial or plant cells.

By engineering gro-1 to be (1) expressed from a bacterial promoter known to stimulate transcription in the organism to be tested, (2) properly translated to generate an intact GRO-1 peptide, and (3) placing the cells in an otherwise toxic concentration of herbicide, one can identify cells that have been transformed with DNA by virtue of their resistance to herbicide. By "promoter" is intended to a nucleic acid sequence that functions to direct transcription of a downstream coding sequence. The promoter, together with other transcriptional and translational regulatory nucleic acid sequences, (also termed as "control sequences") are necessary for the expression of a DNA sequence of interest.

Transformation of bacterial cells is accomplished by one of several techniques known in the art, not limited to electroporation, or chemical transformation (see, for example, Ausubel (ed.) (1994) *Current Protocols in Molecular Biology* (John Wiley and Sons, Inc., Indianapolis, Ind.)). Markers conferring resistance to toxic substances are useful in identifying transformed cells (having taken up and expressed the test DNA) from non-transformed cells (those not containing or not expressing the test DNA).

Transformation of plant cells can be accomplished in a similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The gro-1 gene of the invention may be modified to obtain or enhance expression in plant cells. The herbicide resistance sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a transcriptional and translational termination region (i.e., termination region) functional in plants. The cassette may additionally contain at least one additional gene to be co-transformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Often, such constructs will also contain 5' and 3' untranslated regions. Such constructs may contain a 'signal sequence' or 'leader sequence' to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this transport typically involves secretion into the Golgi apparatus, with some resulting glycosylation. By "leader sequence" is intended any sequence that, when translated, results in an amino acid sequence sufficient to trigger co-translational transport of the peptide chain to a subcellular organelle. Thus, this sequence includes leader sequences targeting transport and/or glycosylation by passage into the endoplasmic reticulum, passage to vacuoles, plastids including chloroplasts, mitochondria, and the like. It is also possible to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens,* such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plants and produce fertile seeds (e.g., Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of the transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-bome transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. In some embodiments, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of the heterologous gene(s) in the plant genome is confirmed by various methods such as analysis of nucleic acids, proteins and metabolites associated with the integrated gene.

PCR analysis is a rapid method to screen transformed cells, tissue or shoots for the presence of the incorporated gene(s) at the earlier stage before transplanting into the soil (Sambrook and Russell (2001) *Molecular Cloning: A Laboratory Manual.* Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}P$ target DNA fragment to confirm the integration of introduced gene in the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures (Sambrook and Russell, 2001, supra). Expression of RNA encoded by gro-1 is then tested by hybridizing the filter to a radioactive probe derived from a GDC, by methods known in the art (Sambrook and Russell, 2001, supra)

Western blot and biochemical assays and the like may be carried out on the transgenic plants to determine the presence of protein encoded by the herbicide resistance gene by standard procedures (Sambrook and Russell, 2001, supra) using antibodies that bind to one or more epitopes present on the herbicide resistance protein.

The following examples are offered by way of illustration and not by way of limitation.

EXPERIMENTAL

EXAMPLE 1

Isolation of ATX4133

ATX4133 was isolated by plating samples of soil on Enriched Minimal Media (EMM) containing glyphosate as the sole source of phosphorus. Since EMM contains no aromatic amino acids, a strain must be resistant to glyphosate in order to grow on this media.

Two grams of soil were suspended in approximately 30 ml of water, and sonicated for 30 seconds in a sonicating water bath. The sample was vortexed for 5 seconds and permitted to settle for 60 seconds. This process was repeated 3 times. 100 µl of this suspension was added to 3 ml of EMM supplemented with 4 mM glyphosate (pH 6.0). EMM contains (per 900 mls): 10 g sucrose, 2 g NaNO$_3$, 1.0 ml 0.8 M MgSO$_4$, 1.0 ml 0.1 M CaCl$_2$, 1.0 ml Trace Elements Solution (In 100 ml of 1000× solution: 0.1 g FeSO$_4$.7H$_2$O, 0.5 mg CuSO$_4$.5H$_2$O, 1.0 mg H$_3$BO$_3$, 1.0 mg MnSO$_4$.5H$_2$O, 7.0 mg ZnSO$_4$.7H$_2$O, 1.0 mg MoO$_3$, 4.0 g KCl). The culture was shaken on a tissue culture roller drum for eleven days at 21° C. and then 100 µl was used to inoculate 3 ml of fresh EMM containing 4 mM glyphosate as the only phosphorus source. After eight days, 100 µl was used to inoculate another fresh 3 ml culture. After nine days, the culture was plated onto solid media by streaking a 1 µl loop onto the surface of an agar plate containing EMM agar containing 5 mM glyphosate as the sole phosphorus source. After four days, colonies were replated for isolation onto EMM containing 5 mM glyphosate as the sole phosphorus source. One particular strain, designated ATX4133, was selected due to its ability to grow in the presence of high glyphosate concentrations. On Luria Bertani (LB) agar, colonies are white, circular, pinsize to 1 mm and stain Gram negative.

To test for its ability to degrade glyphosate, a 3 ml culture of ATX4133 in EMM media containing 1 mM glyphosate as the sole phosphorus source was inoculated. After incubating for six days at 21° C. on a tissue culture roller drum, ATX4133 cells were harvested by centrifuging the culture at 19600×g for 5 minutes and removing the supernatant. ATX4133 supernatant was filtered using a 0.45 µm nylon filter, and 5 µl was applied to an HPLC column (Dionex AminoPac PA10 analytical (and guard) column, anion exchange resin; Dionex Corporation). The column was equilibrated with 150 mM sodium hydroxide and eluted with a sodium acetate gradient of 150-300 mM sodium acetate. Glyphosate was detected with an electrochemical detector (Dionex model ED40). Results are shown in Table 1. Column 1 shows EC detection of glyphosate, column 2 shows µCi of $^{14}C$ glyphosate detected by scintillation counting of collected fractions. ATX4133 growth results in a reduction in the amount of glyphosate in the broth compared to a control strain.

TABLE 1

Peak height of glyphosate detected by HPLC on culture broths

|  | Gly Peak | Gly Pk µCi |
|---|---|---|
| Media Control | 1.71 | 0.0171 |
| Negative Strain | 1.68 | 0.0168 |
| ATX4133 | 0.87 | 0.0087 |

EXAMPLE 2

Isolation of ATX4145

ATX4145 was isolated by plating samples of soil on Enriched Minimal Media (EMM) containing glyphosate as the sole source of phosphorus. Since EMM contains no aromatic amino acids, a strain must be resistant to glyphosate in order to grow on this media.

Two grams of soil were suspended in approximately 30 ml of water, and sonicated for 30 seconds in a sonicating water bath. The sample was vortexed for 5 seconds and permitted to settle for 60 seconds. This process was repeated 3 times. 100 µl of this suspension was added to 3 ml of EMM supplemented with 4 mM glyphosate (pH 6.0). EMM contains (per 900 mls): 10 g sucrose, 2 g NaNO$_3$, 1.0 ml 0.8 M MgSO$_4$, 1.0 ml 0.1 M CaCl$_2$, 1.0 ml Trace Elements Solution (In 100 ml of 1000×solution: 0.1 g FeSO$_4$.7H$_2$O, 0.5 mg CuSO$_4$.5H$_2$O, 1.0 mg H$_3$BO$_3$, 1.0 mg MnSO$_4$.5H$_2$O, 7.0 mg ZnSO$_4$.7H$_2$O, 1.0 mg MoO$_3$, 4.0 g KCl). The culture was shaken on a tissue culture roller drum for sixteen days at 21° C. and then 100 µl was used to inoculate 3 ml of fresh EMM containing 4 mM glyphosate as the only phosphorus source. After five days, 100 µl was used to inoculate another fresh 3 ml culture. After sufficient growth, the culture was plated onto solid media by streaking a 1 µl loop onto the surface of an agar plate containing EMM agar containing 5 mM glyphosate as the sole phosphorus source and stored at 21° C. The culture was then replated for isolation. One particular strain, designated ATX4145, was selected due to its ability to grow in the presence of high glyphosate concentrations. On LB agar, colonies are white, circular, pinsize to 1 mm and stain Gram negative.

To test for its ability to degrade glyphosate, a 3 ml culture of ATX4145 in EMM media containing 1 mM glyphosate as the sole phosphorus source was inoculated. After incubating for six days at 21° C. on a tissue culture roller drum, ATX4145 cells were harvested by centrifuging the culture at 19600×g for 5 minutes and removing the supernatant. ATX4145 supernatant was filtered using a 0.45 µm nylon filter, and 5 µl was applied to an HPLC column (Dionex AminoPac PA10 analytical (and guard) column, anion exchange resin; Dionex Corporation). The column was equilibrated with 150 mM sodium hydroxide and eluted with a sodium acetate gradient of 150-300 mM sodium acetate. Glyphosate was detected with an electrochemical detector (Dionex model ED40). Results are shown in Table 2. Column 1 shows EC detection of glyphosate, column 2 shows µCi of $^{14}C$ glyphosate detected by scintillation counting of collected fractions. ATX 4155 growth results in a reduction in the amount of glyphosate in the broth compared to a control strain.

TABLE 2

Peak height of glyphosate detected by HPLC on culture broths

|  | Gly Peak | Gly Pk µC |
|---|---|---|
| Media Control | 1.71 | 0.0171 |
| Negative Strain | 1.68 | 0.0168 |
| ATX4145 | 0.62 | 0.0062 |

EXAMPLE 3

Identification of Strains ATX4133 and ATX4145

The identity of the strains ATX 4133 and ATX4145 were determined by sequencing of the 16S rDNA region as known in the art. Genomic DNA was isolated from strains Gly13 and Gly25 using methods described in "Current Protocols in Molecular Biology". Pelleted cells were resuspended in TE buffer, and treated with proteinase K. The lysate was extracted with CTAB and phenol/chloroform/isoamyl alcohol as known in the art. The resultant DNA was precipitated with isopropanol, and resuspended in TE buffer. 100 ng DNA from each strain was used as template for PCR. The 16S ribosomal RNA gene was amplified by PCR, and the resultant 16S PCR products sequenced directly. A combination of database searching and multiple sequence aligrnents identified the strain pAX4133 as a *Rhizobium* sp., while pAX4145 was identified as *Brevundimonas vesicularis*.

EXAMPLE 4

Preparation and Screening of Cosmid Libraries

Total DNA was extracted from cultures of ATX4133 and ATX4145 using methods commonly known in the art. The DNA was partially digested with restriction enzyme Sau3A 1 and ligated with SuperCos (Stratagene) vector fragment according to the manufacturer's directions. Ligation products were packaged into phage particles using GigaPack III XL packaging extract (Stratagene), transfected into *E. coli* XL1 Blue MRF' cells, and plated on LB agar containing 50 µg/ml kanamycin to select for colonies containing cosmids. Independent libraries were produced from each strain. For each library approximately 1100 colonies were picked for screening.

Colonies were grown in rich liquid medium containing 50 µg/ml kanamycin, then pinned onto M63 agar medium containing 50 µg/ml kanamycin and 7 mM glyphosate. M63 agar medium contains 100 mM $KH_2PO_4$, 15 mM $(NH_4)_2SO_4$, 50 µM $CaCl_2$, 1 µM $FeSO_4$, 50 µM $MgCl_2$ 55 mM glucose, 25 mg/liter L-proline, 10 mg/liter thiamine HCl, 20 mg/liter chloramphenicol, 0.1 mM IPTG, sufficient NaOH to adjust the pH to 7.0, and 15 g/liter agar. Several colonies which grew in the presence of 7 mM glyphosate were identified from each library. Cosmid DNA was prepared from each of these colonies and re-transformed into *E. coli* XL1 Blue MRF' cells. In each case cells retransformed with cosmid DNA grew on M63 medium in the presence of 5 mM glyphosate while cells containing empty SuperCos vector did not.

One cosmid was selected for further characterization from each library. These cosmids were transformed into *E. coli* aroA⁻, a strain in which the native aroA gene, encoding EPSP synthase, has been deleted. This strain cannot grow on M63 medium because it requires exogenously supplied aromatic amino acids. The presence of cosmids pAX255 or pAX256 did not complement the aroA⁻ phenotype, indicating that the cosmids do not contain EPSP synthase genes.

EXAMPLE 5

Identification of gro-1 in Cosmid pAX255

Cosmid pAX255 was subjected to in vitro transposon mutagenesis using an EZ::TN Insertion Kit (Epicentre, Madison, Wis.) and the manufacturer's protocol. This process randomly inserts a transposon fragment into the cosmid DNA and thus randomly disrupts the function of genes in the cosmid. This particular transposon contains a gene encoding resistance to trimethoprim, so transposon insertion clones may be selected by the ability to grow in the presence of that antibiotic. The locations of the transposon insertions may be determined by restriction fragment mapping or by sequencing with primers which anneal in the transposon. Transposon insertion clones of pAX255 were plated on M63 medium containing 5 mM glyphosate. Three clones were found that had lost the ability to grow in the presence of glyphosate, indicating that the transposon had disrupted the gene responsible for resistance.

The DNA sequence was determined for the region of pAX255 containing the transposon insertions using sequencing methods well known in the art. An open reading frame (ORF) of 831 nucleotides was identified (SEQ ID NO:1). Analysis of the sequence from transposon insertion clones demonstrated that all three insertions which disrupted glyphosate resistance were located within the ORF.

EXAMPLE 6

Identification of gro-2 in Cosmid pAX256

Cosmid pAX256 was subjected to in-vitro transposon mutagenesis as described in Example 5. Transposon insertion clones of pAX256 were plated on M63 medium containing 5 mM glyphosate. Four clones were found that had lost the ability to grow in the presence of glyphosate, indicating that the transposon had disrupted the gene responsible for resistance.

The DNA sequence was determined for the region containing the transposon insertions using sequencing methods well known in the art. An open reading frame (ORF) of 831 nucleotides was identified and designated gro-2 (SEQ ID NO:2). Analysis of the sequence from transposon insertion clones demonstrated that all four insertions that disrupted glyphosate resistance were located within the ORF.

The DNA sequences of gro-1 and gro-2 are 97% identical, differing by 20 nucleotides throughout the length of the two genes. The predicted amino acid sequences encoded by gro-1 and gro-2 are 100% identical and are presented in SEQ ID NO:3. gro-1 was compared to sequences in the public databases using the BLASTP search program from NCBI. The alignment of FIG. 5 shows proteins that are highly homologous to GRO-1 and GRO-2.

EXAMPLE 7.

Engineering of gro-1 for Expression of GRO-1 Protein in *E. coli*

The gro-1 ORF was amplified from pAX255 by polymerase chain reaction using methods well known in the art, ligated into an expression under the control of the Tac promoter, and transformed into *E. coli* DH5α cells. The DNA sequence of the ORF was determined to ensure against PCR-induced errors, and the resulting plasmid was designated pAX650. Plasmid pAX650 containing the gro-1 ORF was deposited at the Agricultural Research Service Culture Collection (NRRL) on Nov. 17, 2004, and assigned Accession No. NRRL B-30787.

EXAMPLE 8 gro-1 Confers Resistance to High Levels of Glyphosate pAX650 was tested for the ability to grow on M63 medium in the presence of glyphosate using cells containing empty vector as a control. The results are summarized in Table 3.

TABLE 3

Glyphosate resistance of pAX650 containing gro-1

| Glyphosate concentration (mM) | Vector control | gro-1 |
|---|---|---|
| 0 | ++ | ++ |
| 5 | − | ++ |
| 10 | − | ++ |
| 20 | − | + |

EXAMPLE 9

Purification of gro-1 Expressed as a 6×His-tagged Protein in *E. coli*

The gro-1 coding region (831 nucleotides) was amplified by PCR using PfuUltra™ DNA polymerase (Stratagene). Oligonucleotides used to prime PCR were designed to introduce restriction enzyme recognition sites near the 5' and 3' ends of the resulting PCR product. The resulting PCR product was digested with Sal I. The digested product was cloned into the 6×His-tag expression vector pRSF1b (Novagen), prepared by digestion with Sal I. The resulting clone, pAX1900, contained GRO-1 in the same translational reading frame as, and immediately C-terminal to, the 6×His tag. General strategies for generating such clones, and for expressing proteins containing 6×His-tag are well known in the art.

The ability of this clone to confer glyphosate resistance was confirmed by plating cells onto M63 media containing 5 mM glyphosate. pAX1900 was able to grow at this concentration of glyphosate, while vector controls did not grow.

Induction of GRO-1 protein from pAX1900 resulted in high levels of expression of GRO-1 protein on an SDS-PAGE protein gel. GRO-1 protein can be isolated by purification of the induced GRO-1 protein by chromatography on, for example, Ni-NTA Superflow Resin (Qiagen), as per manufacturer's instructions.

EXAMPLE 10

Design of syngro-1

A synthetic DNA sequence encoding gro-1 was designed. The resulting gene, syngro-1 (SEQ ID NO:4), contained in pAX254, encodes the identical amino acid sequence as the gro-1 gene, but lacks any substantial open reading frames other than the gro-1 ORF.

EXAMPLE 11

Expression of syngro-1 in *E. coli*

The syngro-1 ORF was cloned into the plasmid vector pUC19 by methods known in the art. The 876 nucleotide Pst I to BamH I fragment from pAX254, containing the syngro-1 ORF, was cloned into the Pst I to BamH I sites of pUC 19. The resulting plasmid was designated pAX285. The syngro-1 ORF is oriented in pAX285 such that transcription is driven by the lac promoter. This cloning strategy also fortuitously introduced a stop codon into the 5' end of lacZ so that syngro-1 is not expressed as a fusion protein with lacZ but is translationally coupled to the truncated lacZ ORF. The plasmid pAX285 was transformed into *E. coli* strain DH5α and streaked onto M63 agar plates supplemented with 50 μg/ml carbenicillin and 1 mM IPTG (to ensure expression from the lac promoter). DH5α cells harboring empty pUC19 plasmid were used as a control. The results are summarized in Table 4.

TABLE 4

Glyphosate Resistance encoded by syngro-1

| Glyphosate Concentration (mM) | Vector Control | pAX285 |
|---|---|---|
| 0 | ++ | ++ |
| 5 | − | ++ |
| 10 | − | ++ |

EXAMPLE 12

Engineering gro-1 for Plant Transformation

The gro-1 open reading frame (ORF) is amplified by polymerase chain reaction from a full-length cDNA template. Hind III restriction sites are added to each end of the ORF during PCR. Additionally, the nucleotide sequence ACC is added immediately 5' to the start codon of the gene to increase translational efficiency (Kozak (1987) 15:8125-8148; Joshi (1987) *Nucleic Acids Research* 15:6643-6653). The PCR product is cloned and sequenced, using techniques well known in the art, to ensure that no mutations are introduced during PCR.

The plasmid containing the gro-1 PCR product is digested with, for example, Hind III and the fragment containing the intact ORF is isolated. In this example, the fragment is cloned into the Hind III site of a plasmid such as pAX200, a plant expression vector containing the rice actin promoter (McElroy et al. (1991) *Molec. Gen. Genet.* 231:150-160) and the PinII terminator (An et al. (1989) *The Plant Cell* 1:115-122). The promoter—gene—terminator fragment from this intermediate plasmid is then subcloned into a plasmid such as pSB11 (Japan Tobacco, Inc.) to form a final plasmid, referred to herein as pSB11GRO. pSB11GRO is organized such that the 3.91 kb DNA fragment containing the promoter—gro-1—terminator construct may be excised by double digestion with appropriate restriction enzymes and also used for transformation into plants by, for example, aerosol beam injection. The structure of pSB11GRO is verified by restriction digests and gel electrophoresis and by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plating on media containing spectinomycin. Plasmid pSB11GRO carries antibiotic resistance but is a narrow host range plasmid and cannot replicate in *Agrobacterium*. Antibiotic resistant colonies arise when pSB11GRO integrates into the broad host range plasmid, such as pSB1, through homologous recombination. The resulting cointegrate product is verified by Southern hybridization. The *Agrobacterium* strain harboring the cointegrate product can then be used to transform maize, for example, by the PureIntro method (Japan Tobacco).

EXAMPLE 13

Transformation of gro-1 into Plant Cells

Maize ears are best collected 8-12 days after pollination. Embryos are isolated from the ears, and embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express GRO-1 in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| Components | per liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH 5.8 with 1N KOH/1N KCl, add Gelrite (Sigma) to 3 g/L, and autoclave. After cooling to 50° C., add 2 ml/L of a 5 mg/ml stock solution of silver nitrate (Phytotechnology Labs). Recipe yields about 20 plates.

EXAMPLE 14

Transformation of gro-1 into Maize Plant Cells by *Agrobacterium*-Mediated Transformation Ears are best collected 8-12 days after pollination. Embryos are isolated from the ears, and those embryos 0.8-1.5 mm in size are preferred to be used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated nucleic acid molecule selected from the group consisting of:
   a) a nucleic acid molecule comprising the nucleotide sequence of SEQ ID NO:1, 2, or 4;
   b) the herbicide resistance nucleotide sequence of the DNA insert of the plasmid deposited as Accession No. NRRL B-30787, or a complement thereof; and,
   c) a nucleic acid molecule which encodes a polypeptide comprising the amino acid sequence of SEQ ID NO:3.

2. The isolated nucleic acid molecule of claim 1, wherein said nucleotide sequence is a synthetic sequence that has been designed for expression in a plant.

3. The nucleic acid molecule of claim 2, wherein said synthetic sequence has an increased GC content.

4. A vector comprising the nucleic acid molecule of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A transformed seed comprising the nucleic acid molecule of claim 1.

12. A method for producing a polypeptide with herbicide resistance activity, comprising culturing the host cell of claim 6 under conditions in which a nucleic acid molecule encoding the polypeptide is expressed, said polypeptide being selected from the group consisting of:
   a) a polypeptide comprising the amino acid sequence of SEQ ID NO:3;
   b) a polypeptide encoded by the nucleic acid sequence of SEQ ID NO:1, 2, or 4; and,
   c) a polypeptide that is encoded by the herbicide resistance nucleotide sequence of the DNA insert of the plasmid deposited as Accession No. NRRL B-30787.

13. A method for conferring resistance to an herbicide in a plant, said method comprising transforming said plant with a DNA construct, said construct comprising a promoter that drives expression in a plant cell operably linked with a nucleotide sequence comprising SEQ ID NO:1, 2, or 4, wherein said nucleic acid molecule encodes a polypeptide with herbicide resistance activity, and regenerating a transformed plant.

14. The method of claim 13, wherein said herbicide is a glyphosate.

15. A plant having stably incorporated into its genome a DNA construct comprising a nucleotide sequence that encodes a protein having herbicide resistance activity, wherein said nucleotide sequence is selected from the group consisting of:
   a) a nucleotide sequence of SEQ ID NO:1, 2, or 4;
   b) a nucleotide sequence encoding a polypeptide comprising an amino acid sequence of SEQ ID NO:3; and,
   c) the herbicide resistance nucleotide sequence of the DNA insert of the plasmid deposited as Accession No. NRRL B-30787;

wherein said nucleotide sequence is operably linked to a promoter that drives expression of a coding sequence in a plant cell.

16. The plant of claim 15, wherein said plant is a plant cell.

* * * * *

UNITED STATES PATENT AND TRADEMARK OFFICE
CERTIFICATE OF CORRECTION

PATENT NO.        : 7,488,866 B2                                         Page 1 of 1
APPLICATION NO. : 11/312866
DATED             : February 10, 2009
INVENTOR(S)       : Hammer et al.

It is certified that error appears in the above-identified patent and that said Letters Patent is hereby corrected as shown below:

Column 9,
Line 25, "$\geqq 90\%$" should read --$\geq 90\%$--.

Column 16,
Line 17, "bome" should read --borne--.

Column 19,
Line 46, "aligrnents" should read --alignments--.

Signed and Sealed this

Thirtieth Day of June, 2009

JOHN DOLL
*Acting Director of the United States Patent and Trademark Office*